United States Patent
Sakata et al.

(10) Patent No.: US 7,436,929 B2
(45) Date of Patent: Oct. 14, 2008

(54) RADIOGRAPHIC SYSTEM

(75) Inventors: Atsushi Sakata, Kanagawa (JP);
Toshiyoshi Yamamoto, Hyogo (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 11/720,570

(22) PCT Filed: Dec. 1, 2005

(86) PCT No.: PCT/JP2005/022092

§ 371 (c)(1),
(2), (4) Date: May 31, 2007

(87) PCT Pub. No.: WO2006/059685

PCT Pub. Date: Jun. 8, 2006

(65) Prior Publication Data

US 2008/0089473 A1      Apr. 17, 2008

(30) Foreign Application Priority Data

Dec. 1, 2004   (JP)   ............... 2004-348774

(51) Int. Cl.
*H05G 1/38* (2006.01)
(52) U.S. Cl. .................... 378/96; 378/38; 378/98.8
(58) Field of Classification Search ............. 378/38–40, 378/91, 96, 98–98.8, 207
See application file for complete search history.

(56) References Cited

U.S. PATENT DOCUMENTS 5,600,699 A   2/1997   Suzuki et al.
5,664,001 A   9/1997   Tachibana et al.

FOREIGN PATENT DOCUMENTS

| JP | 2000-175907 | 6/2000 |
| JP | 3291406 | 3/2002 |
| JP | 3465582 | 8/2003 |

OTHER PUBLICATIONS

International Search Report from the corresponding PCT/JP2005/022092, mailed Jan. 17, 2006.

*Primary Examiner*—Jurie Yun
(74) *Attorney, Agent, or Firm*—Hamre, Schumann, Mueller & Larson, P.C.

(57) ABSTRACT

A radiographic system is provided, which is capable of displaying brightness of laterally corresponding points with equivalent brightness, when an object having equivalent texture structures or micro areas of equivalent X-ray transmittance at laterally symmetric positions. The radiographic system includes an exposure time deriving section that obtains a period during which the object has been exposed to X-rays in a process of generating each charge signal output from an X-ray image detecting section based on vertical transfer information held at the vertical transfer information holding section, a correction coefficient deriving section that obtains a correction coefficient for correcting the value of an image signal obtained by being converted from each charge signal, based on the exposure time, and an image generating section that generates an image signal from the charge signal output from the X-ray image detecting section and the correction coefficient.

2 Claims, 13 Drawing Sheets

RADIOGRAPHIC SYSTEM

TECHNICAL FIELD

The present invention relates to a radiographic system that photographs a transmitted X-ray image by placing an object including the teeth, the jawbone, and the like in a human head between X-ray generating means and image pickup means opposed thereto, and rotating the X-ray generating means and the image pickup means in a dental clinic or the like.

BACKGROUND ART

Recently, as a radiographic system, a digital system using a solid-state image pickup device such as a charge-coupled device (hereinafter, referred to as an "X-ray CCD"), instead of a conventional silver-halide film (hereinafter, referred to as a film), is spreading. According to the digital system, compared with a conventional film system, there are a number of advantages: 1) an image can be observed in real time; 2) a developing device and disposal of waste liquid are not required; 3) a photo-detecting sensitivity is high, and an X-ray irradiation amount is low; 4) image processing such as enlargement and gray-scale correction is easy; 5) there is no change in a captured image with the passage of time, so that the captured image before treatment easily can be compared with that after the treatment; 6) storage space can be saved; etc.

However, when an attempt is made so as to photograph an X-ray image using such a solid-state image pickup device and using the same control method as that for ordinary photographing, it is necessary to prepare a solid-state image pickup device having an effective image pickup area with a horizontal width of 300 mm and a height of 150 mm comparable to that of a film, so that it is difficult to realize such photographing.

In order to photograph an X-ray image using a solid-state image pickup device, a photographing method has been proposed in which photographing is performed while charges in the solid-state image pickup device are transferred in accordance with the movement of an object moving in front of the solid-state image pickup device. According to this method, the solid-state image pickup device may have a width of an X-ray beam passing through a secondary slit of a radiographic system in a horizontal direction.

In a conventional radiographic system (Conventional Example 1), based on data on the previously set changing condition of a movement speed of a film during a period from the start of photographing to the end thereof at a time of photographing with a film (hereinafter, referred to as film-advance speed data), each time for the movement of a film by the width of a charge generating device constituting a solid-state image pickup device during a period from the start of photographing to the end thereof is obtained. For each time for the movement of a film during photographing, vertical transfer is performed in which charges in a vertical shift register are transferred by one stage toward a horizontal shift register in the solid-state image pickup device, and thereafter, a charge signal in the horizontal shift register is output to the outside of the solid-state image pickup device (e.g., see Patent Document 1).

Furthermore, as another conventional example (Conventional Example 2), there also is a radiographic system in which, in the same way as in the above-mentioned conventional radiographic system, a timing for transferring charges in a vertical shift register (hereinafter, referred to as vertical transfer) in a solid-state image pickup device is obtained from an angular velocity ω of a rotary arm and a functional value f(θ) responding to a rotation angle θ of the rotary arm to determine a tomographic orbit sequentially during photographing (e.g., see Patent Document 2).

FIG. 12 is a block diagram showing a configuration of a radiographic system as Conventional Example 1.

In FIG. 12, a conventional radiographic system includes an X-ray generating section 2 that generates X-rays, an X-ray CCD 203 that is a solid-state image pickup device, a sensor cassette 202 in which the X-ray CCD 203 is inserted, a cassette mounting section 201 in which the sensor cassette 202 is inserted, a rotary arm 4 that connects the X-ray generating section 2 to the cassette mounting section 201, a photographing operation managing section 204 that generates a signal to be a reference of a drive signal for controlling X-rays, a drive signal control circuit 205 that supplies a drive signal to the X-ray CCD 203 for photographing target teeth, a drive timing information output section 206 that outputs timing information for driving the X-ray CCD 203, a data processing circuit 207 that processes photographed image information, and display means 208 that displays the photographed image.

FIGS. 13A, 13B, and 13C are a front view, a right side view, and a top view, respectively, showing an outer appearance of the radiographic system of Conventional Example 1 shown in FIG. 12.

In FIG. 13, an object 1 is positioned so as to be interposed between the X-ray generating section 2 and the cassette mounting section 201 (X-ray image detecting section 3). The rotary arm 4 that connects the X-ray generating section 2 to the cassette mounting section 201 is supported rotatably by a column 209.

Next, the operation of the radiographic system configured as described above will be described.

As shown in FIG. 13C, the rotary arm 4 rotates clockwise when the periphery of the object 1 is seen from the above.

FIG. 5 is a schematic diagram schematically showing the X-ray CCD 203 (FIG. 12) during rotation. In FIG. 5, cells 114a, 114b that are charge generating devices for converting X-rays into charges are arranged two-dimensionally without any gap to constitute the X-ray CCD 203. FIG. 5 illustrates, as main components of the X-ray CCD 203, a vertical shift register 110 in which cells are connected in a horizontal direction and which transfers charges between the connected cells, and a horizontal shift register 111 in which cells are connected in a vertical direction and which transfers charges between the connected cells. Charges 113a, 113b are generated by X-rays transmitted through micro areas 112a, 112b (also referred to as 112 collectively) of the object to reach the X-ray CCD 203. In FIG. 5, A, B, ..., H are symbols attached accessorily so as to specify a cell in a column direction, and a, b, ..., f are symbols attached accessorily so as to specify a cell in a row direction.

As shown in FIG. 5, when the rotary arm 4 rotates, the micro areas 112 constituting the object 1 are transferred from the left to the right with respect to the X-ray CCD 203 in parallel to the vertical shift register 110.

When the micro area 112a of the object 1 is positioned as illustrated at a certain time, an X-ray transmitted through the micro area 112a reaches the cell 114a, and the charge 113a is generated in the cell 114a. Then, when the micro area 112b is transferred to the illustrated position after the elapse of a certain period, an X-ray transmitted through the micro area 112b reaches the cell 114b, and the charge 113b is generated in the cell 114b.

Herein, when vertical transfer is performed simultaneously when the micro area 112b of the object 1 reaches the illustrated position, the charge 113a is transferred from the cell 114a to the cell 114b, with the result that the charge 113a and the charge 113b are added up in the cell 114b.

The above-mentioned movement and addition of charges are repeated from a time when the micro area 112 reaches the front of a cell in A column d row to a time when the micro area 112 leaves the front of a cell in G column d row, and the charge 113 corresponding to the micro area 112 is transferred to a cell in H column d row in the horizontal shift register 111 and is output from the X-ray CCD 203.

In the above-mentioned process, the timing at which a charge is transferred from a cell to an adjacent cell is obtained previously by the following method.

FIG. 3 is a graph illustrating a method for obtaining a timing at which the vertical transfer of charges in the X-ray CCD 203 is performed. In FIG. 3, a curve 106 represents a temporal change of a relative movement speed of a film with respect to the cassette mounting section 201 (FIG. 12) (hereinafter, referred to as a film-advance speed) from the start of photographing to the end thereof at a time of photographing with a film.

With the width of a cell being w, a time $t_n$ ($n \geq 1$) required for a film to proceed by a distance w, 2w, 3w, . . . , nw, . . . from the start of photographing is obtained. More specifically, the time $t_n$ is obtained so that an area of a region surrounded by an x-axis, the curve 106, a straight line $X=t_n$, and a straight line $X=t_{n-1}$ ($n \geq 1$) becomes w.

With $t_0=0$, the value of a time difference $\Delta t_1, \Delta t_2, \Delta t_3, \ldots, \Delta t_n, \ldots$ is obtained together with the obtained $t_n$ by the following expression.

$$\Delta t_1 = t_1 - t_0, \Delta t_2 = t_2 - t_1, \ldots, \Delta t_n = t_n - t_{n-1}, \ldots$$

Using $\Delta t_n$ thus obtained, a vertical transfer signal 107 is generated at a time interval illustrated in a timing chart of FIG. 4. In FIG. 4, when the vertical transfer signal 107 becomes a High level, a charge is transferred from a cell to an adjacent cell in the vertical shift register 110 (FIG. 5).

Furthermore, in the radiographic system as Conventional Example 2, during X-ray photographing, a frequency of a vertical transfer clock for a shift for controlling the movement of charges in the vertical shift register is obtained from an angular velocity ω of the rotary arm and a rotation angle θ thereof, whereby the movement of a micro area of the object is matched with the movement of a charge corresponding thereto.

Patent Document 1: Japanese Patent No. 3465582 (pages 4-5, FIGS. 1, 2)

Patent Document 2: Japanese Patent No. 3291406 (pages 3-4, FIG. 2)

DISCLOSURE OF INVENTION

Problem to be Solved by the Invention

However, in the case where X-ray photographing is performed with the movement of charges being controlled by the above-mentioned method in the conventional radiographic system, when photographing is performed, corresponding to film-advance speed data for obtaining a tomographic orbit laterally symmetric with respect to a midline of a human face to be an object, the following problem arises. That is, if the obtained X-ray image originally is laterally symmetric with respect to the midline, and the texture structures of portions (hereinafter, referred to as points) corresponding to the right and left sides are the same or the X-ray transmittance thereof is the same, the brightness of the image should be the same; however, actually, the brightness of the image does not become the same.

In terms of the diagnosis using an X-ray image, it is important that the state of an osseous tissue can be estimated more correctly from the lateral symmetry and the brightness of an image.

In an X-ray image, an image in a portion with a low X-ray transmittance of an object is expressed to be lighter, and an image in a portion with a high X-ray transmittance of the object is expressed to be darker. Generally, in an osseous tissue, when bone density is high, an image is expressed to be lighter. When bone density is low, an image is expressed to be darker. Therefore, in two images of osseous tissues photographed under the same X-ray irradiation condition, if one image is darker than the other image, the bone density of the osseous tissue of the darker image is low and can be evaluated and diagnosed to be brittle.

However, in the conventional radiographic system in which the brightness of images may not be the same even with the same bone density or the same X-ray transmittance, or the brightness of images with different bone densities may be the same, exact comparison, evaluation, and diagnosis cannot be performed.

Furthermore, in temporomandibular joint quadrant photographing (TMJ4) that is one X-ray photographing, a photographed image of the left-side temporomandibular joint and a photographed image of the right-side temporomandibular joint are displayed discontinuously. Therefore, the difference in brightness in portions to be the background where an object does not appear is recognized more clearly, which causes doubt as to whether the photographed image of the left-side temporomandibular joint and the photographed image of the right-side temporomandibular joint may not have been photographed under the same condition. Thus, the reliability of photographing itself may decline.

Next, the process by which a problematic phenomenon occurs will be considered.

The film-advance speed is designed so as to be laterally symmetric with respect to a midline as represented by the curve 106 in FIG. 3. That is, the changing condition of a film-advance speed while the X-ray image detecting section 3 (FIG. 13) is transferred from the front of the midline until the end of photographing is arranged in an order temporally opposite to a changing condition of the film-advance speed from the start of photographing until the X-ray image detecting section 3 reaches the front of the midline.

X-ray photographing by the conventional radiographic system is tomography, and the depth of a tomogram varies depending upon the film-advance speed. Thus, in order to obtain tomogram images with the same depth between the right and left under an assumption that the teeth form to be photographed is laterally symmetric, it is necessary that the film is transferred at the same speed.

FIG. 6 is a view displaying an example of an actual X-ray image. An image displayed as an X-ray image generally is expressed to be lighter as the exposure amount of X-rays is smaller.

The width of a panoramic image is assumed to be (2n−1) pixels. A point PL of an m-th pixel from the left of an image in a certain row corresponds to a point PR of an m-th pixel from the right of the image. Portions of an object corresponding to the points PL and PR are placed at substantially the same positions between the right and the left, and a normal healthy osseous tissue would have equivalent texture structures. Therefore, it is desirable that the points PL and PR have the same brightness in the X-ray image.

A description will be made assuming that the X-ray image is output successively from the left column.

In one transmission of a vertical transfer signal, the vertical transfer by one stage of charges is performed, and a charge in each cell in the vertical shift register, closest to the horizontal shift register, is transferred to the horizontal shift register and output from the X-ray CCD 203 (FIG. 12).

That is, the column on the leftmost side of the X-ray image being output in the first transmission of a vertical transfer signal and the width of the X-ray image being (2n−1) pixels mean that the vertical transfer signal is transmitted (2n−1) times during photographing.

Herein, the point PL of the m-th pixel from the left is output by the transmission of a vertical transfer signal of the m-th pixel, and the point PR of the m-the pixel from the right corresponding to the point PL of the m-th pixel from the left is output by the transmission of a (2n−m)-th vertical transfer signal.

Herein, the number of stages of the vertical shift register of the CCD is assumed to be K.

FIG. 7 is a schematic structural view of the X-ray CCD 203 (FIG. 12).

In FIG. 7, the charge representing the point PL (FIG. 6) output with an m-th vertical transfer signal is transferred from a cell in a K-th stage of the vertical shift register 110 to the horizontal shift register 111 with the m-th vertical transfer signal, and is transferred from a cell in a (K−1)-th stage to a cell in the K-th stage of the vertical shift register 110 with an (m−1)-th vertical transfer signal. Thus, the charge is transferred from the cell 104 in the first stage to the cell in the second stage when an (m−K+1)-th vertical transfer signal is transmitted, and the charge appears in the cell 104 in the first stage at a moment when an (m−K)-th vertical transfer signal is transmitted. Accordingly, a period during which the charge representing the point PL remains in the vertical shift register 110 of the CCD corresponds to a period from the time when the (m−K)-th vertical transfer signal is transmitted to the time when the m-th vertical transfer signal is transmitted.

Similarly, a period during which the charge representing the point PR (FIG. 6) remains in the vertical shift register 110 of the CCD corresponds to a period from the time when a (2n−m−K)-th vertical transfer signal is transmitted to the time when a (2n−m)-th vertical transfer signal is transmitted.

These periods will be checked in the graph of FIG. 8. In FIG. 8, a time when a j-th vertical transfer signal is transmitted is represented by $t_j$. The number of stages of the vertical shift register 110 is illustrated to be 5.

In FIG. 8, the speed corresponding to a time $t_m$ is not the same as the speed corresponding to a time $t_{2n-m}$. The time corresponding to the same speed as that of the time $t_m$ is $t_{2n-m-1}$, and hence, the time $t_{2n-m}$ is shifted by one to the right.

In the graph of FIG. 8, when the time difference between $t_{m-k}$ and $t_m$ is compared with the time difference between $t_{2n-m-k}$ and $t_{2n-m}$, the time difference between $t_{m-k}$ and $t_m$ is smaller. The reason for this is as follows: the speed in that time band is higher than the speed in a time band from $t_{2n-m-k}$ to $t_{2n-m}$, so that it takes a shorter time for a charge to proceed by the same distance.

Thus, the charge representing the point PL shown in FIG. 6 remains in the X-ray CCD 203 only for a period of time shorter than that representing the point PR. This shows that a period during which the point PL has been exposed to an X-ray is shorter; consequently, the point PL is expressed to be lighter, compared with the point PR.

The above description similarly applies to the case where the width of a panoramic image obtained by photographing is 2n pixels.

As described above, it is an object of the present invention to provide a radiographic system capable of displaying the brightness of laterally corresponding points with equivalent brightness, when photographing an object having equivalent texture structures or micro areas of equivalent X-ray transmittance at laterally symmetric positions.

Means for Solving Problem

In order to achieve the above object, a first radiographic system according to the present invention includes: an x-ray generating section that generates X-rays; an x-ray image detecting section in which charge generating devices for converting the X-rays into charges are placed in series in a row in a horizontal direction or placed two-dimensionally; a rotary arm that rotates the X-ray generating section and the X-ray image detecting section around an object with the X-ray generating section and the X-ray image detecting section opposed to each other; a vertical transfer information holding section that previously generates and holds vertical transfer information for successively transferring the charges of the charge generating devices in accordance with a relative movement of the object with respect to the X-ray image detecting section involved in the rotation of the rotary arm; a drive control section that controls drive of the X-ray image detecting section while controlling a timing at which vertical transfer is performed based on the vertical transfer information held at the vertical transfer information holding section; an exposure time deriving section that obtains a period during which the object has been exposed to the X-rays in a process of generating each charge signal output from the X-ray image detecting section in the X-ray image detecting section based on the vertical transfer information held at the vertical transfer information holding section; a correction coefficient deriving section that obtains a correction coefficient for correcting a value of an image signal obtained by being converted from each charge signal, based on the exposure time of each charge signal; and an image generating section that generates an image signal from the charge signal output from the X-ray image detecting section and the correction coefficient.

According to the above configuration, the exposure time corresponding to each point in an image is obtained previously, the values of charge signals corresponding to laterally symmetric points are corrected with a ratio of exposure times, and the ratio of brightness between the laterally corresponding points is set to be the same as the ratio of X-ray transmittance of the respective corresponding portions in an object, whereby the brightness of the laterally corresponding points can be displayed with the equivalent brightness.

Furthermore, in order to achieve the above object, a second radiographic system according to the present invention includes: an x-ray generating section that generates X-rays; an x-ray image detecting section in which charge generating devices for converting the X-rays into charges are placed in series in a row in a horizontal direction or placed two-dimensionally; a rotary arm that rotates the X-ray generating section and the X-ray image detecting section around an object with the X-ray generating section and the X-ray image detecting section opposed to each other; a vertical transfer information generating section that successively generates, during photographing, vertical transfer information for successively transferring the charges of the charge generating devices in accordance with a relative movement of the object with respect to the X-ray image detecting section involved in the rotation of the rotary arm; a drive control section that controls drive of the X-ray image detecting section while controlling a timing at which vertical transfer is performed based on the vertical transfer information generated by the vertical transfer information generating section; a vertical transfer information recording section that records a time interval at which the vertical transfer information is generated by the vertical transfer information generating section during photographing; an exposure time deriving section that obtains a period during which the object has been exposed to the X-rays in a process of generating each charge signal output from the X-ray image detecting section in the X-ray image detecting section based on the time interval, at which vertical transfer is performed, recorded in the vertical transfer information recording section; a correction coefficient deriving section that obtains a correction coefficient for correcting a value of an image signal obtained by being converted from each charge signal, based on the exposure time of each charge signal; and an image generating section that generates an image signal from the charge signal output from the X-ray image detecting section and the correction coefficient.

According to the above configuration, the exposure time corresponding to each point in an image is obtained from a rotation state of the rotary arm during photographing, the values of charge signals corresponding to laterally symmetric points are corrected with a ratio of exposure times, and the ratio of brightness between the laterally corresponding points is set to be the same as the ratio of X-ray transmittance of the respective corresponding portions in an object, whereby the brightness of the laterally corresponding points can be displayed with the equivalent brightness.

Effects of the Invention

According to the present invention, values of charge signals corresponding to laterally symmetric points in an image are corrected with an exposure time ratio. Thus, the following special effect is exhibited: an image can be generated and displayed, in which it can be evaluated and diagnosed that portions of an object corresponding to laterally symmetric points in an image have equivalent texture structures or equivalent X-ray transmittance when the brightness of the points is equivalent, and it can be evaluated and diagnosed that there is a difference in texture structures or X-ray transmittance when there is a difference in brightness.

DESCRIPTION OF THE INVENTION

Hereinafter, the present invention will be described by way of preferable embodiments with reference to the drawings.

Embodiment 1

Figure 1:
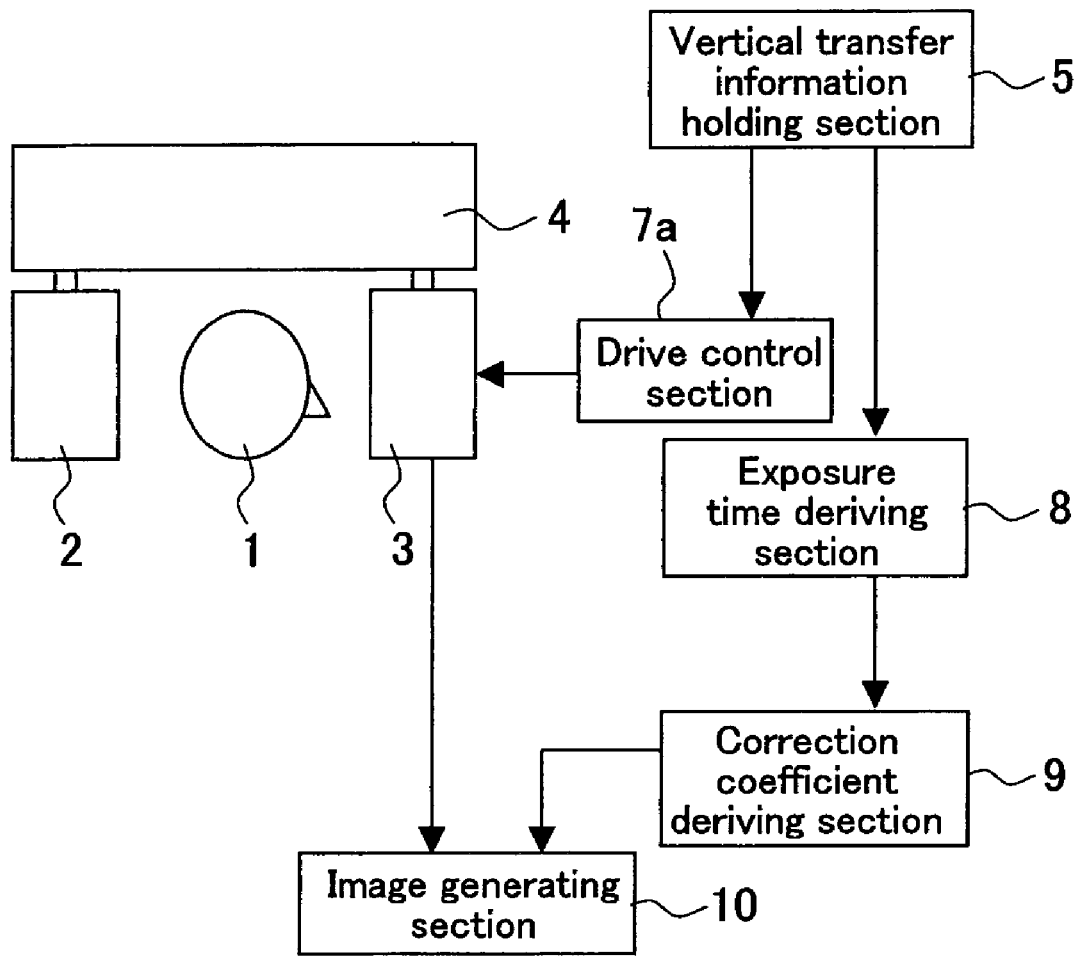
FIG. 1 is a block diagram showing one exemplary configuration of a radiographic system according to Embodiment 1 of the present invention.
Figure 12:
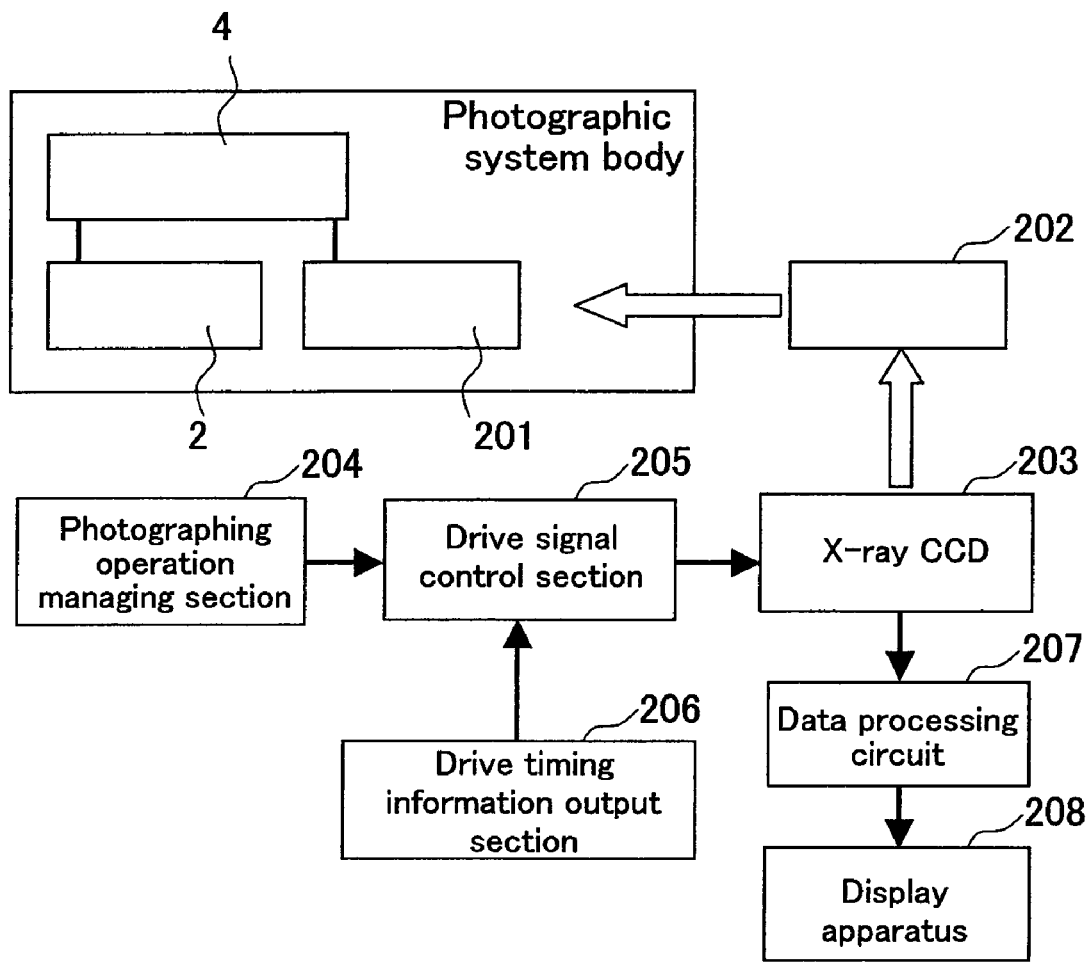
FIG. 12 is a block diagram showing a configuration of a radiographic system of Conventional Example 1.
Figure 13A:
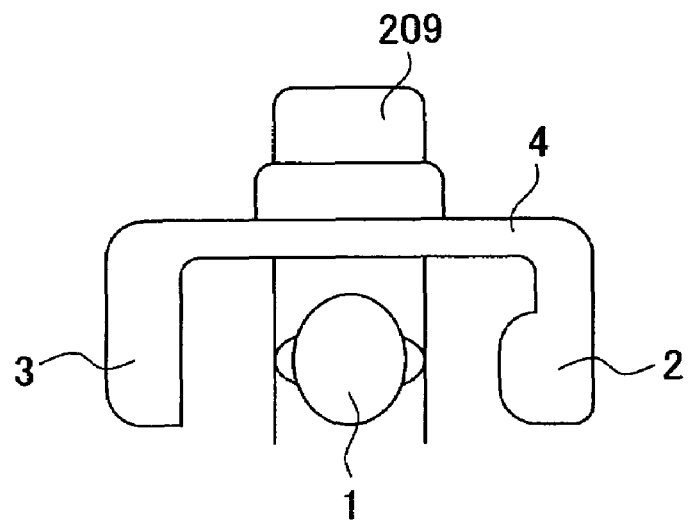
FIG. 13 shows a front view A, a right side view B, and a top view C showing an outer appearance of the radiographic system of Conventional Example 1 shown in FIG. 12.
Figure 13B:
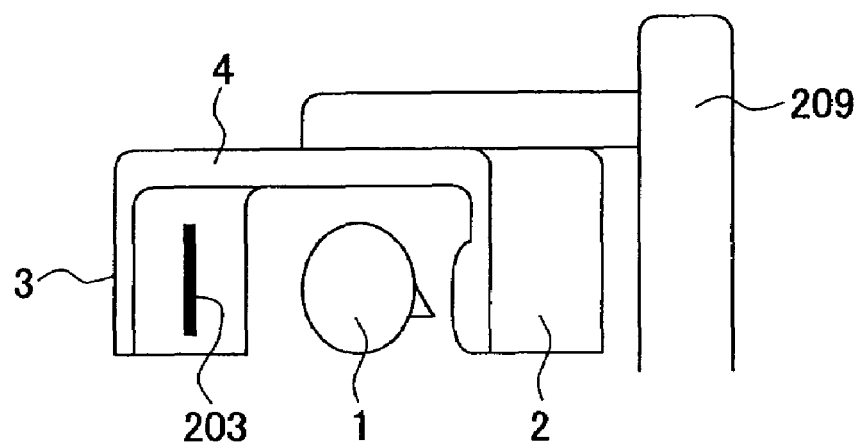
Figure 13C:
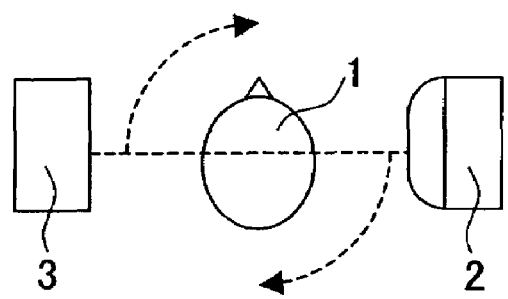

FIG. 1 is a block diagram showing one exemplary configuration of a radiographic system according to Embodiment 1 of the present invention. In FIG. 1, components having the same configurations and functions as those in FIGS. 12 and 13 referred to in the description of Conventional Example 1 are denoted with the same reference numerals as those therein, and the description thereof will be omitted.

In FIG. 1, in addition to the X-ray generating section 2, the X-ray image detecting section 3, and the rotary arm 4 similar to those in the conventional example, the radiographic system of Embodiment 1 includes a vertical transfer information holding section 5 that previously generates and holds vertical transfer information for performing vertical transfer of charges in the X-ray CCD (not shown, corresponding to reference numeral 203 in FIG. 12) in accordance with the relative movement of the object 1 with respect to the X-ray image detecting section 3 involved in the rotation of the rotary arm 4, a drive control section 7a that controls the drive of the X-ray image detecting section while controlling the timing at which the vertical transfer is performed based on the vertical transfer information held at the vertical transfer information holding section 5, an exposure time deriving section 8 that obtains a period during which the object 1 has been exposed to X-rays in a process of generating, in the X-ray image detecting section 3, each charge signal output from the X-ray image detecting section 3 based on the vertical transfer information held at the vertical transfer information holding section 5, a correction coefficient deriving section 9 that obtains a correction coefficient for correcting the value (brightness) of an image signal obtained by converting each charge signal with an A/D converter based on the exposure time of each charge signal (correcting the value of an image signal according to the exposure time), and an image generating section 10 that generates an image signal from a charge signal and a correction coefficient output from the X-ray image detecting section 3.

Next, the operation of the radiographic system of the embodiment configured as described above will be described.

Figure 3:
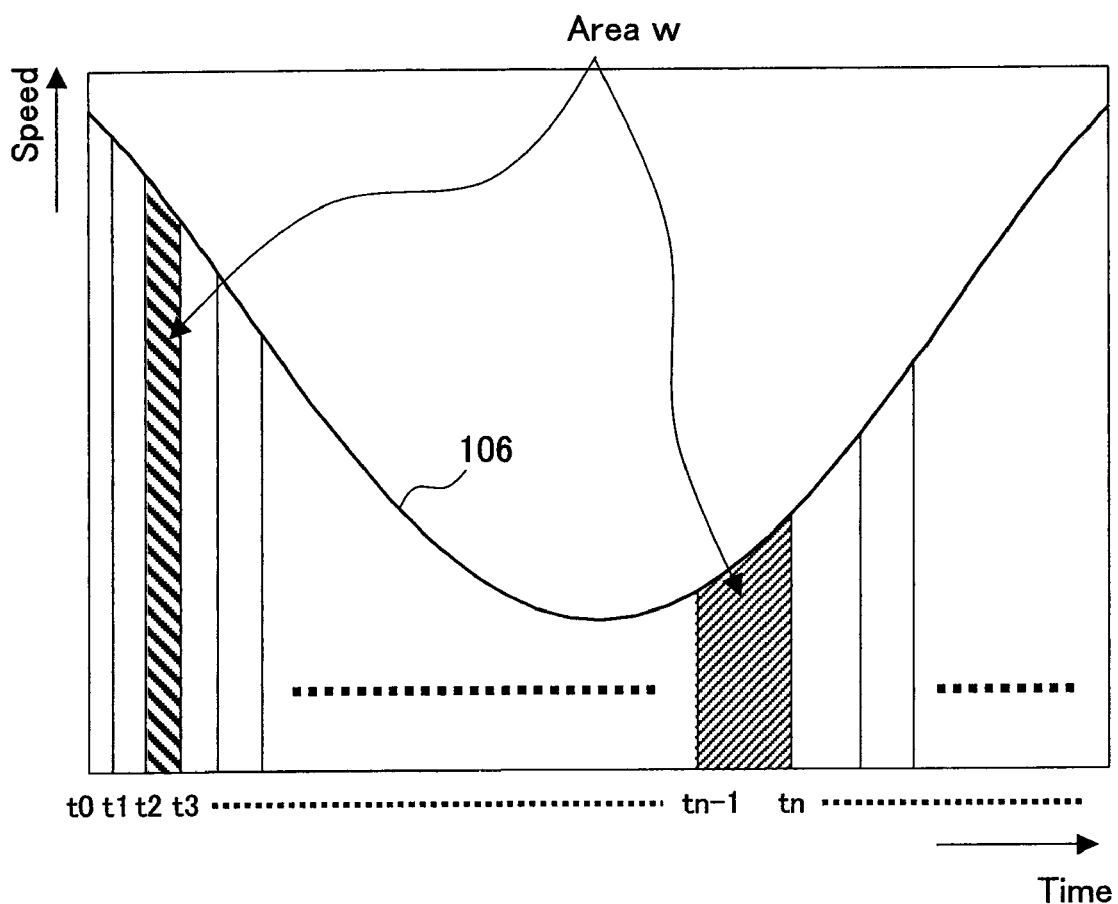
FIG. 3 is a graph illustrating a method for obtaining a timing at which vertical transfer of charges in an X-ray CCD is performed.

Prior to photographing, vertical transfer signal transmission time intervals (vertical transfer information) $\Delta t_1$, $\Delta t_2$, $\Delta t_3$ ... $\Delta t_n$ ... for transferring charge signals in the vertical shift register of the X-ray CCD in accordance with the movement of the micro areas of the object during photographing are obtained previously based on film-advance speed data and the like, and held at the vertical transfer information holding section 5. The vertical transfer signal transmission time intervals $\Delta t_1, \Delta t_2, \Delta t_3 \ldots \Delta t_n \ldots$ correspond to time differences in the conventional example described with reference to FIGS. 3 and 4.

At the time of photographing, the object 1 is placed between the X-ray generating section 2 and the X-ray detecting section 3. The X-ray generating section 2 and the X-ray image detecting section 3 are rotated around the object 1 with the rotary arm 4. During rotation, the X-ray generating section 2 radiates X-rays, and the X-ray image detecting section 3 generates charges corresponding to the amount of X-rays transmitted through the object 1 and reaching the photo-detecting plane of the X-ray image detecting section 3.

Figure 4:
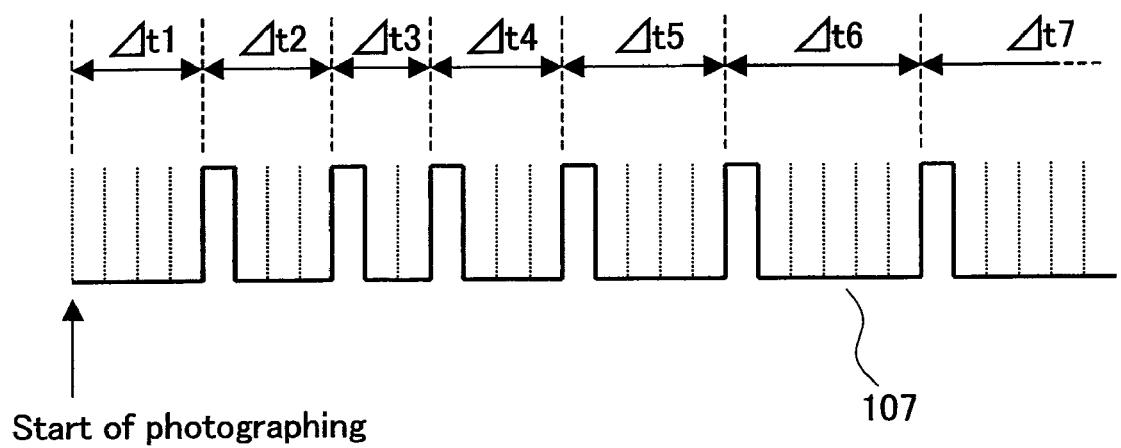
FIG. 4 is a timing chart showing a vertical transfer signal controlled at each time interval.
Figure 5:
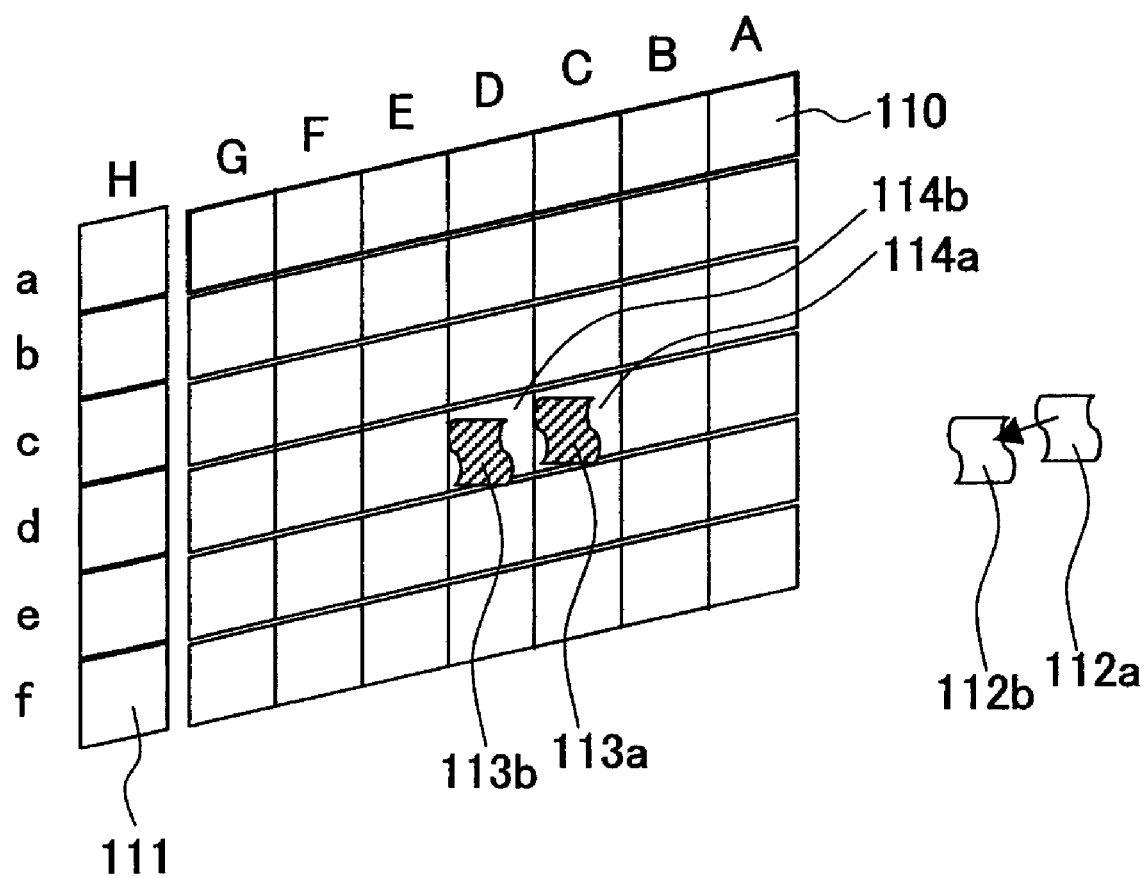
FIG. 5 is a schematic diagram showing a relationship between charges in a vertical shift register in an X-ray CCD and micro areas of an object.
Figure 6:
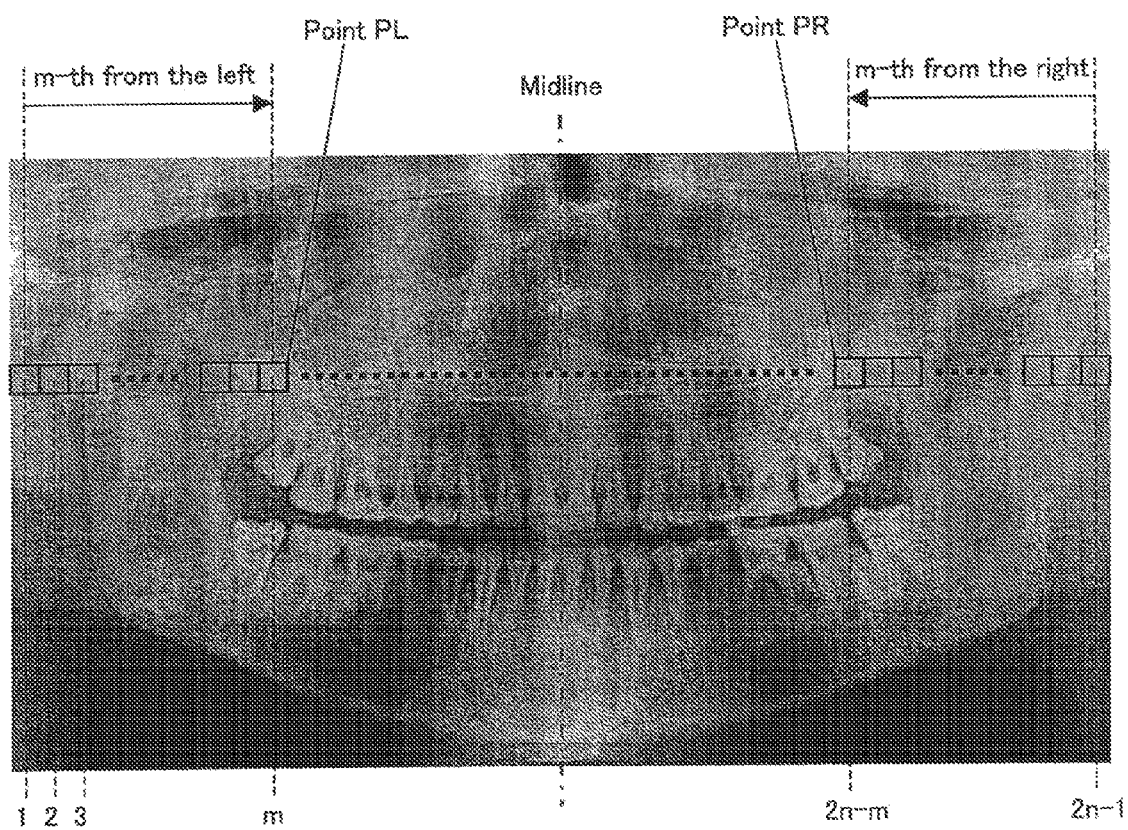
FIG. 6 is a view showing an example of an X-ray image.

During the irradiation of the X-rays, based on the vertical transfer signal transmission time intervals held at the vertical transfer information holding section 5, the drive control section 7a transmits a vertical transfer signal to the X-ray image detecting section 3 at time intervals shown in FIG. 4. When the vertical transfer signal 107 shown in FIG. 4 becomes a High level, a vertical transfer signal for transferring a charge from a cell to an adjacent cell in the vertical shift register of the X-ray CCD is transmitted from the drive control section 7a.

After that, the drive control section 7a controls the transfer of charges in the horizontal shift register of the X-ray CCD, and a charge signal is output from the X-ray image detecting section 3 to the image generating section 10.

The exposure time deriving section 8 obtains a period during which the object 1 has been exposed to X-rays in the process of generating each charge signal output from the X-ray image detecting section 3 in the X-ray image detecting section 3 based on the vertical transfer signal transmission time intervals held at the vertical transfer information holding section.

Figure 7:
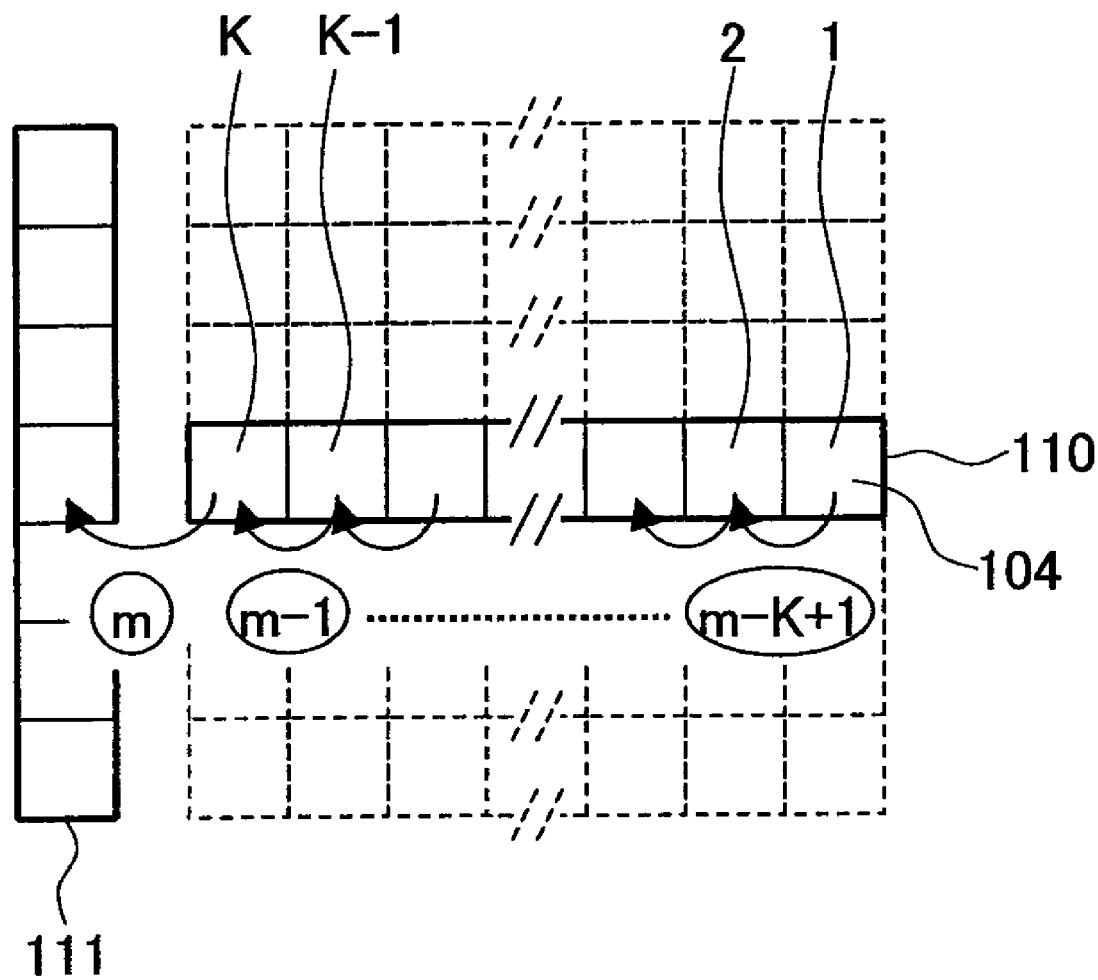
FIG. 7 is a schematic structural view of the X-ray CCD.
Figure 8:
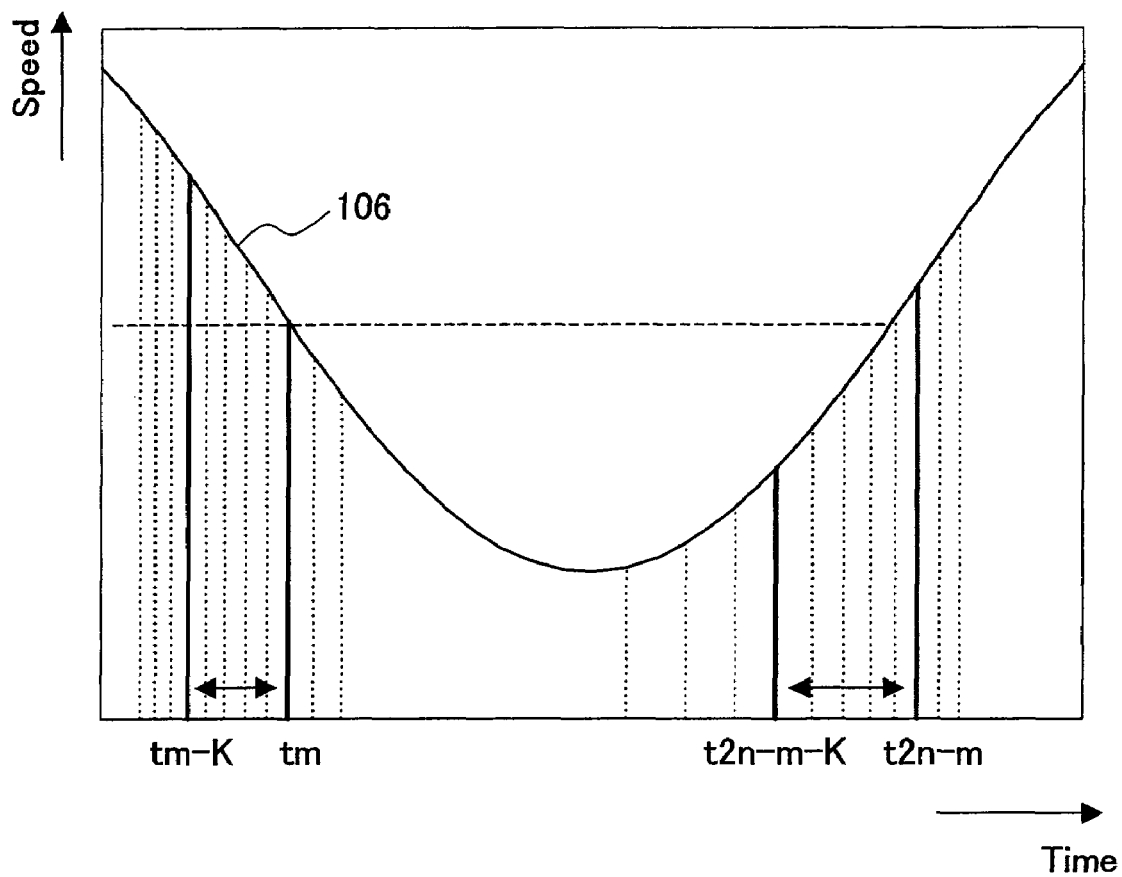
FIG. 8 is a graph illustrating a cause for the occurrence of a problem in a conventional radiographic system.

Herein, the way of obtaining an exposure time in the exposure time deriving section 8 will be described with reference to FIG. 7. It is assumed that the number of stages of the vertical shift register of the X-ray CCD in the X-ray image detecting section 3 is K.

Regarding the charge signal, one column of an X-ray image is output from the X-ray CCD every time one vertical transfer signal is transmitted. The charge in the cell 104 in the K-stage is transferred to the horizontal shift register 111 by the transmission of a first vertical transfer signal after the start of photographing, and an image signal in a first column is output from the X-ray CCD. Similarly, an image signal in a second column is output after the transmission of a second vertical transfer signal. That is, a charge signal output in an n-th time to be an image signal in an n-th column is transferred from the vertical shift register 110 to the horizontal shift register 111 by the transmission of the n-th vertical transfer signal, and output from the X-ray CCD.

A charge signal is generated by the exposure to an X-ray in the vertical shift register 110.

The charge signal output from the x-ray CCD with the n-th vertical transfer signal is generated in the cell 104 in the first stage in the X-ray CCD immediately after an (n−K)-th vertical transfer signal is transmitted. This charge remains in the cell 104 in the first stage until an (n−K+1)-th vertical transfer signal is transmitted, and hence, is a vertical transfer signal transmission time interval $\Delta t_{n-K+1}$ obtained previously. Thus, assuming that a period of an exposure to an X-ray corresponding to the charge signal output in the n-th time is $I_n$, $I_n$ is obtained by the following expression.

$$I_n = \Delta t_{n-K+1} + \Delta t_{n-K+2} + \ldots + \Delta t_{n-1} + \Delta t_n$$

Regarding points at laterally symmetric positions with respect to a midline in an X-ray image, the correction coefficient deriving section 9 obtains a correction coefficient for obtaining a value to be obtained if the exposure time of the point on the left side is equivalent to that of the point on the right side, based on the exposure time at the point on the right side with respect to the midline in an object.

Herein, the way of obtaining a correction coefficient in the correction coefficient deriving section 9 will be described.

In the present embodiment, regarding the X-ray image, it is assumed that the number of points of a horizontal width is (2n−1) pixels, and an n-th pixel from an end corresponds to the midline. In the X-ray image, the correction coefficient at a point of an m-th pixel from the left side of the image is represented by km.

A point PRm of an m-th pixel from the right side of the image corresponding to a point PLm of an m-th pixel from the left side of the image is a (2n−m)-th pixel from the left side of the image. Thus, the exposure time of the point PLm is $I_m$, and the exposure time of the point RPm is $I_{2n-m}$. Accordingly, the correction coefficient of the point PLm is represented by $k_m$, and the correction coefficient of the point PRm is represented by $k_{2n-m}$, and respective correction coefficients are obtained by the following expressions.

$$k_m = I_{2n-m}/I_m$$

$$k_{2n-m} = I_{2n-m}/I_{2n-m} = 1$$

These correction coefficients are obtained with respect to m in a range of 1 to n−1.

The image generating part 10 performs correction and generation of an image. Regarding the correction, assuming that the value of an image signal before correction corresponding to the point PLm of the m-th pixel from the left of the image is $V_m$, and the value of an image signal after correction is $V_m'$, $$V_m' = k_m \times V_m$$

and assuming that the value of an image signal before correction of the point PRm corresponding to the point PLm is $V_{2n-m}$, and the value after correction is $V_{2n-m}'$, $$V_{2n-m}' = k_{2n-m} \times V_{2n-m}.$$

Consequently, the image signal is corrected to the value obtained when the exposure time of the point PLm on the left side is equivalent to that of the point PRm on the right side.

A method for calculating a correction coefficient may be as follows:

$$k_m = I_m/I_m = 1$$

$$k_{2n-m} = I_m/I_{2n-m}$$

based on the exposure time at a point on the left side with respect to the midline in the object 1.

Alternatively, a correction coefficient may be obtained by:

$$I_{AVE} = (I_m + I_{2n-m})/2$$

$$k_m = I_{AVE}/I_m$$

$$k_{2n-m} = I_{AVE}/I_{2n-m}$$

where $I_{AVE}$ represents an average of exposure times at laterally symmetric points.

Alternatively, a correction coefficient may be obtained by:

$$k_m = IT_m/I_m$$

$$k_{2n-m} = IT_m1_{2n-m}$$

where a distribution of an exposure time is obtained so that the change of an exposure time of each pixel from the start of photographing to the end of thereof is laterally symmetric with respect to a midline, and is smooth in the midline portion, and the exposure time at an m-th point from the left side of the image obtained from the exposure distribution is $IT_m$ (=$IT_{2n-m}$).

A correction coefficient may be obtained by obtaining a midline position of an image from film-advance speed data, and assuming that pixels on the right and left sides at an equal distance from the midline position correspond to lateral symmetric positions. Hereinafter, an exemplary method for obtaining a midline position of an image from film-advance speed data will be described.

Film-advance speed data at an arbitrary photographing time and an image output during photographing based on the film-advance speed data will be considered. The film-advance speed data is symmetric with respect to a time for photographing a midline with respect to a portion for photographing teeth, in terms of characteristics of panoramic photography. Thus, a portion to be symmetric with respect to a certain time is obtained from the film-advance speed data at an arbitrary photographing time, a distance by which a film proceeds from the start of photographing to the certain time is obtained, and a value S is obtained by dividing the distance by a length corresponding to a lateral width of one pixel of an image, whereby a pixel in an S-column from the end in an image at the start of photographing is determined to correspond to a midline.

As described above, the exposure time deriving section 8 and the correction coefficient deriving section 9 are provided, an exposure time at each point in an image is obtained, a correction coefficient is obtained with respect to each of laterally symmetric two points of the image, using the values of exposure times corresponding to the two points, and an value of an image signal corresponding to each point of the image is corrected. Consequently, when an object having equivalent texture structures or micro areas of equivalent X-ray transmittance at laterally symmetric positions is photographed, the brightness of laterally corresponding points can be displayed with the equivalent brightness.

Embodiment 2

Figure 2:
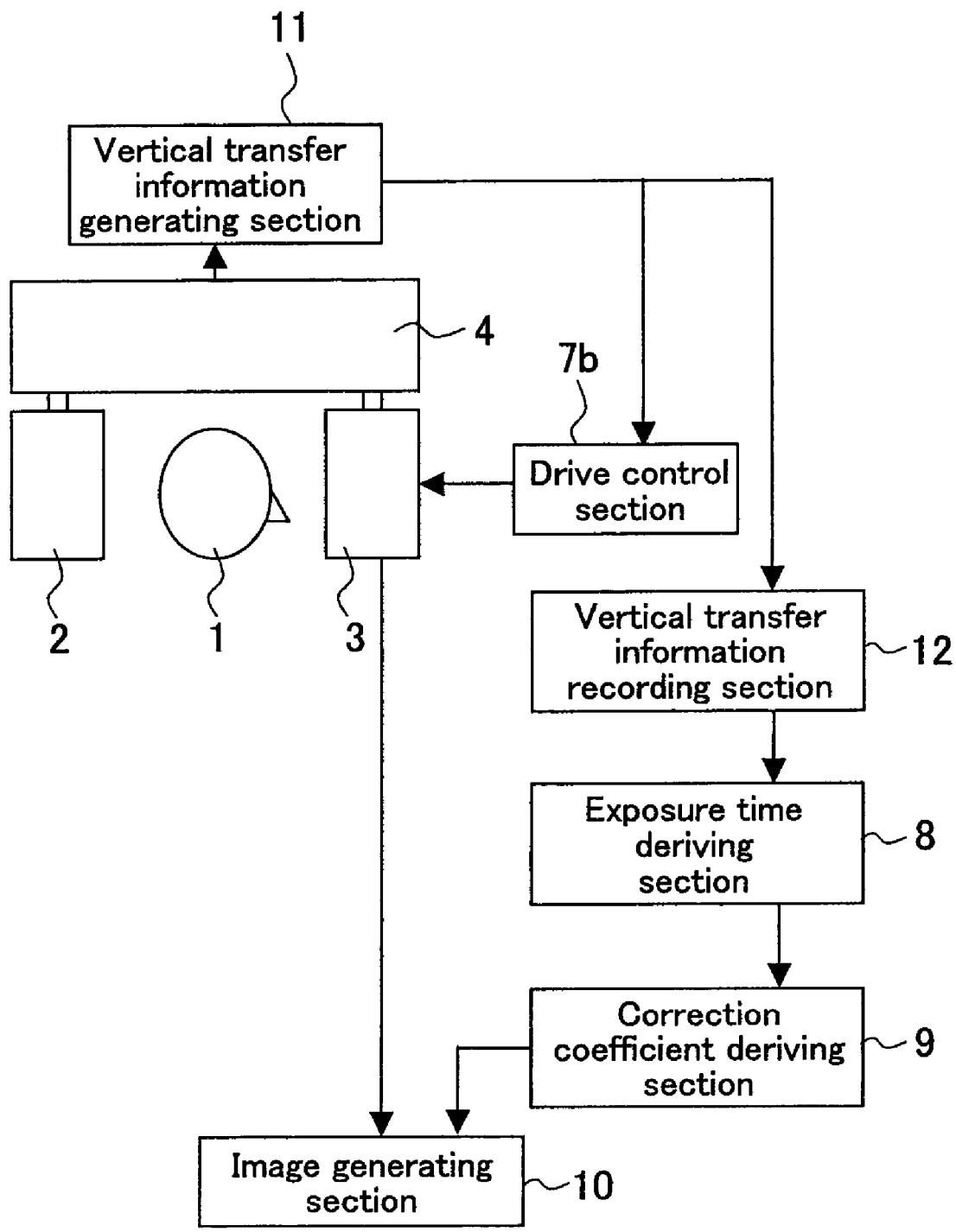
FIG. 2 is a block diagram showing one exemplary configuration of a radiographic system according to Embodiment 2 of the present invention.

FIG. 2 is a block diagram showing one exemplary configuration of a radiographic system according to Embodiment 2 of the present invention. In FIG. 2, components having the same configurations and functions as those in FIG. 1 referred to in the description of Embodiment 1 are denoted with the same reference numerals as those therein, and the description thereof will be omitted.

In FIG. 2, in addition to the X-ray generating section 2, the X-ray image detecting section 3, the rotary arm 4, the exposure time deriving section 8, the correction coefficient deriving section 9, and the image generating section 10 in Embodiment 1, the radiographic system of the present embodiment includes a drive control section 7b, a vertical transfer information generating section 11 that detects a rotation angle of the rotary arm 4 from the start of photographing and an angular velocity of the rotary arm 4 changing during rotation at all times, sequentially generates vertical transfer information for successively transferring charge signals in the X-ray detecting section 3 in accordance with the relative movement of the object 1 with respect to the X-ray image detecting section 3 involved in the rotation of the rotary arm 4 during photographing, and outputs a timing for vertical transfer to the drive control section 7b, and a vertical transfer information recording section 12 that records time intervals of the vertical transfer timing output by the vertical transfer information generating section 11 during photographing.

The present embodiment is different from Embodiment 1 in the following point. In Embodiment 1, a vertical transfer signal transmission time interval is obtained previously before photographing and held at the vertical transfer information holding section 5. The transmission of a vertical transfer signal is controlled during photographing, and an exposure time corresponding to each charge signal is obtained by the exposure time deriving section 8 from the vertical transfer signal transmission time intervals held at the vertical transfer information holding section 5. In the present embodiment, the vertical transfer information generating section 11 determines a timing at which vertical transfer is performed based on the rotation state of the rotary arm 4 at all times during photographing, thereby controlling the transmission of a vertical transfer signal. Furthermore, the vertical transfer information recording section 12 records time intervals at which vertical transfer is performed during photographing, and the exposure time deriving section 8 obtains an exposure time of each pixel from the time intervals recorded in the vertical transfer information recording section 12.

Next, the operation of the radiographic system of the present embodiment configured as described above will be described.

First, the object 1 is placed between the X-ray generating section 2 and the X-ray image detecting section 3. The X-ray generating section 2 and the X-ray image detecting section 3 are rotated around the object 1 by the rotary arm 4. During rotation, the X-ray generating section 2 radiates X-rays, and the X-ray image detecting section 3 generates charges corresponding to the amount of the X-rays transmitted through the object 1 and reaching a photo-detecting plane of the X-ray image detecting section 3.

Figure 9:
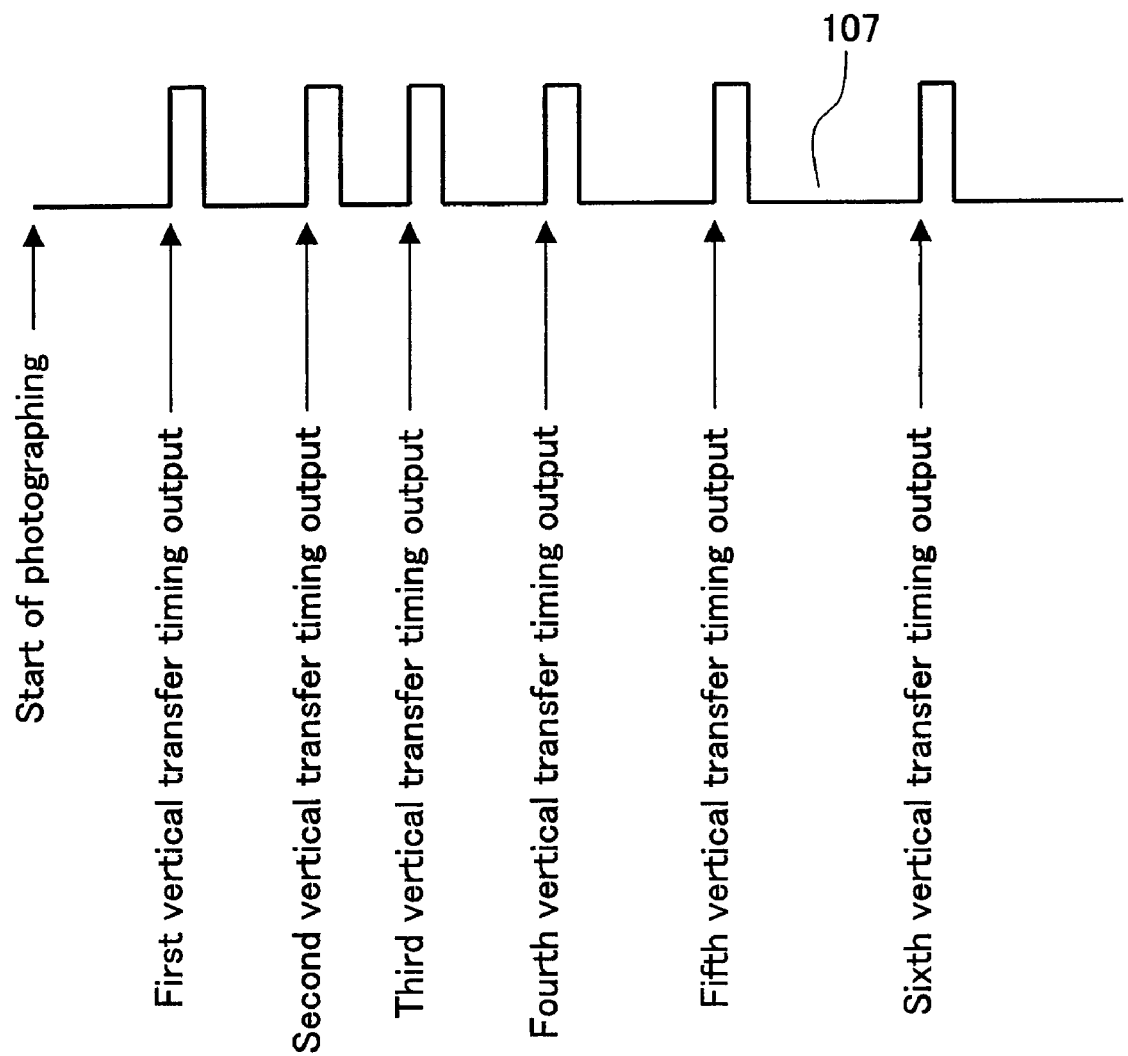
FIG. 9 is a timing chart showing a vertical transfer signal controlled at each vertical transfer timing in a radiographic system according to Embodiment 2 of the present invention.

While the X-rays are being radiated, the drive control section 7b transmits a vertical transfer signal 107 shown in FIG. 9 in accordance with a vertical transfer execution timing output from the vertical transfer information generating section 11, and causes the X-ray CCD of the X-ray image detecting section 3 to perform vertical transfer. In FIG. 9, when the vertical transfer signal 107 becomes a High level, a charge is transferred from a cell to an adjacent cell in the vertical shift register of the X-ray CCD.

Furthermore, the drive control section 7 controls the transfer of the charges in a horizontal shift register of the X-ray CCD, and causes the X-ray image detecting section 3 to output charge signals to the image generating section 10.

Next, the output process of a vertical transfer execution timing by the vertical transfer information generating section 11 will be described.

Figure 10:
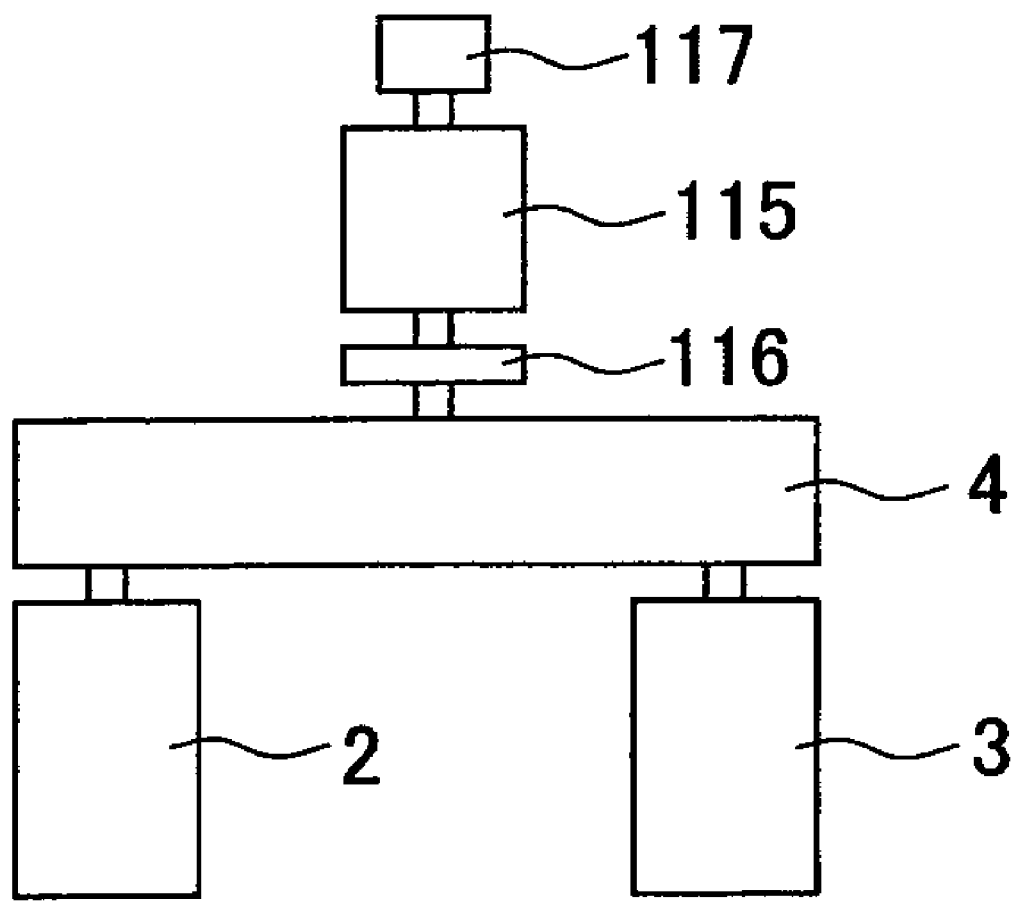
FIG. 10 is a block diagram showing a main configuration of a vertical transfer information generating section of the radiographic system according to Embodiment 2 of the present invention.

FIG. 10 is a block diagram showing the main configuration of the vertical transfer information generating section 11 of the radiographic system according to Embodiment 2. The same components as those in FIG. 2 are denoted with the same reference numerals as those therein.

In FIG. 10, the vertical transfer information generating section 11 includes a rotation control section 115 that rotates the rotary arm 4, a rotation angle detector 116 that sequentially detects and outputs a rotation angle θ from the start of photographing of the rotary arm 4, and an angular velocity detector 117 that sequentially detects and outputs an angular velocity ω of the rotary arm 4.

Figure 11:
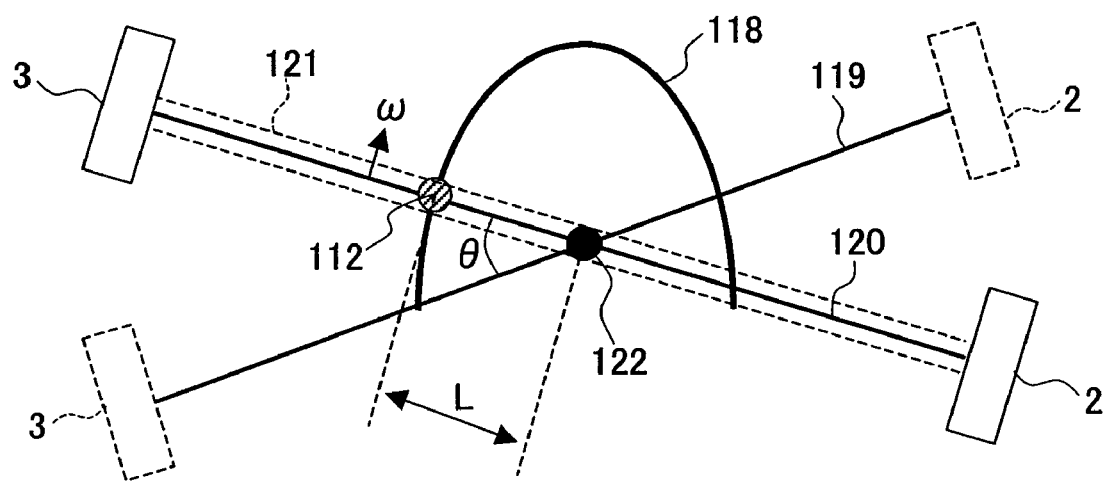
FIG. 11 is a schematic view showing a positional relationship among an X-ray generating section of the radiographic system according to Embodiment 2 of the present invention, an X-ray image detecting section thereof, and an object.

FIG. 11 is a schematic view showing a positional relationship among the X-ray generating section 2, the X-ray image detecting section 3, and the object 1 during photographing. In FIG. 11, reference numeral 118 denotes a teeth shape to be the object 1 that is recorded and held previously by the radiographic system or is obtained by measurement before photographing, 112 denotes a micro area in the object 1, 119 denotes a straight line connecting the X-ray generating section 2 to the center of the X-ray image detecting section at the start of photographing, 120 denotes a straight line connecting the X-ray generating section 2 to the center of the X-ray image detecting section 3 at a time when the rotary arm during photographing is rotated by an angle θ, 121 denotes an irradiation field of X-ray beams, and 122 denotes a rotation center.

An X-ray image of the micro area 112 in the object 1 that enters the irradiation field of the X-ray beams is projected to the X-ray image detecting section 3 to be photographed.

Next, the micro area 112 that is in the irradiation field of the X-ray beams at a time when the rotary arm 4 rotates by the angle θ from the start of photographing will be considered.

It is assumed that a rotation angular velocity of the rotary arm 4 at a time when the rotary arm 4 rotates by the angle θ is ω. Furthermore, the teeth form does not have a circular shape with a rotation center 122 of the rotary arm 4 being the center. Therefore, a distance L from the rotation center 122 to the micro area 112 changes with the change in the angle θ, and the distance L can be obtained by a function f(θ) of the angle θ: L=f(θ). Thus, the movement speed of the micro area 112 is f(θ)×ω.

Herein, it is considered that X-rays generated from the X-ray generating section 2 and reaching the X-ray CCD of the X-ray image detecting section 3 are substantially parallel radiation. Thus, the movement speed of an X-ray image on the X-ray image detecting section 3 of the micro area 112 on the object 1 also is f(θ)×ω. Assuming that the width of one cell of the X-ray image detecting section 3 is w, a time taken for the X-ray image to pass one cell is w/(f(θ)×ω). Thus, the vertical transfer information generating section 11 (FIG. 2) outputs a vertical transfer execution timing for each time w/f(θ)×ω).

The vertical transfer information recording section 12 measures time intervals at which the vertical transfer execution timing is transmitted from the vertical transfer information generating section 11 successively from the start of photographing, and recorded to be held.

The exposure time deriving section 8 obtains a period during which each charge signal output from the X-ray image detecting section 3 has been generated by an exposure to an X-ray in the X-ray image detecting section 3, based on the transmission time intervals of the vertical transfer execution timing held at the vertical transfer information recording section 12.

When assuming that a transmission time interval from the transmission of an (n−1)-th vertical transfer execution timing to the transmission of an n-th vertical transfer execution timing recorded and held at the vertical transfer information recording section 12 is $\Delta t_n$, the way of obtaining an exposure time in the exposure time deriving section 8, the way of obtaining a correction coefficient in the correction coefficient deriving section 9, and the way of executing correction and generating an image in the image generating section 10 are the same as those in Embodiment 1. Therefore, the detailed description thereof will be omitted.

Furthermore, a method for calculating another correction coefficient also is the same as that in Embodiment 1.

As described above, according to the present embodiment, there are the following advantages in addition to the advantage in Embodiment 1.

By providing the vertical transfer information generating section 11 and the vertical transfer information recording section 12, and monitoring the rotation of the rotary arm 4 during photographing to generate and record vertical transfer information, an appropriate exposure time can be obtained even in the case where the rotation control of the rotary arm 4 does not have high precision and the rotation speed of the rotary arm 4 varies, and even in the case where the rotation speed of the rotary arm 4 shifts from the rotation speed set in terms of design due to the disorder that is not expected in terms of design.

INDUSTRIAL APPLICABILITY

The radiographic system according to the present invention can make the values of pixels in portions with equivalent texture structures or equivalent X-ray transmittance in an object uniform, and can evaluate whether the bone density in one portion is equal to or higher/lower than that in the other portion, for example, based on the comparison of the brightness of pixels. Thus, the radiographic system according to the present invention is effective for image reading diagnosis based on the comparison of a plurality of sites.

Furthermore, the correction method of the present invention also is effective for the application to temporomandibular joint bisecting photographing and temporomandibular joint quadrant photographing of photographing right and left temporomandibular joints.

The invention claimed is:

1. A radiographic system, comprising:

an x-ray generating section that generates X-rays;

an x-ray image detecting section in which charge generating devices for converting the X-rays into charges are placed in series in a row in a horizontal direction or placed two-dimensionally;

a rotary arm that rotates the X-ray generating section and the X-ray image detecting section around an object with the X-ray generating section and the X-ray image detecting section opposed to each other;

a vertical transfer information holding section that previously generates and holds vertical transfer information for successively transferring the charges of the charge generating devices in accordance with a relative movement of the object with respect to the X-ray image detecting section according to the rotation of the rotary arm;

a drive control section that controls drive of the X-ray image detecting section while controlling a timing at which vertical transfer is performed based on the vertical transfer information held at the vertical transfer information holding section;

an exposure time deriving section that obtains a period during which the object has been exposed to the X-rays in a process of generating each charge signal output from the X-ray image detecting section in the X-ray image detecting section based on the vertical transfer information held at the vertical transfer information holding section;

a correction coefficient deriving section that obtains a correction coefficient for correcting a value of an image signal obtained by being converted from each charge signal, based on the exposure time corresponding to each charge signal; and an image generating section that generates an image signal from the charge signal output from the X-ray image detecting section and the correction coefficient.

2. A radiographic system, comprising:

an x-ray generating section that generates X-rays;

an x-ray image detecting section in which charge generating devices for converting the X-rays into charges are placed in series in a row in a horizontal direction or placed two-dimensionally;

a rotary arm that rotates the X-ray generating section and the X-ray image detecting section around an object with the X-ray generating section and the X-ray image detecting section opposed to each other;

a vertical transfer information generating section that successively generates, during photographing, vertical transfer information for successively transferring the charges of the charge generating devices in accordance with a relative movement of the object with respect to the X-ray image detecting section according to the rotation of the rotary arm;

a drive control section that controls drive of the X-ray image detecting section while controlling a timing at which vertical transfer is performed based on the vertical transfer information generated by the vertical transfer information generating section;

a vertical transfer information recording section that records a time interval at which the vertical transfer information is generated by the vertical transfer information generating section during photographing;

an exposure time deriving section that obtains a period during which the object has been exposed to the X-rays in a process of generating each charge signal output from the X-ray image detecting section in the X-ray image detecting section based on the time interval, at which vertical transfer is performed, recorded in the vertical transfer information recording section;

a correction coefficient deriving section that obtains a correction coefficient for correcting a value of an image signal obtained by being converted from each charge signal, based on the exposure time corresponding to each charge signal; and an image generating section that generates an image signal from the charge signal output from the X-ray image detecting section and the correction coefficient.

* * * * *